US008002691B2

(12) United States Patent
Peters et al.

(10) Patent No.: US 8,002,691 B2
(45) Date of Patent: *Aug. 23, 2011

(54) FLUID PRESSURE GENERATING MEANS

(75) Inventors: William Suttle Peters, Auckland (NZ); Hans Hansforth Henrichsen, Wellongong (AU); Peter Andrew Watterson, Denistone (AU)

(73) Assignee: Sunshine Heart Company Pty Ltd. (AU)

( * ) Notice: Subject to any disclaimer, the term of this patent is extended or adjusted under 35 U.S.C. 154(b) by 95 days.

This patent is subject to a terminal disclaimer.

(21) Appl. No.: 11/870,968

(22) Filed: Oct. 11, 2007

(65) Prior Publication Data

US 2008/0027270 A1   Jan. 31, 2008

Related U.S. Application Data (63) Continuation of application No. 10/380,789, filed as application No. PCT/AU02/00974 on Jul. 22, 2002, now Pat. No. 7,306,558.

(30) Foreign Application Priority Data

Jul. 30, 2001 (AU) .......................................... 6690

(51) Int. Cl.
A61N 1/362 (2006.01)

(52) U.S. Cl. .............................. 600/16; 600/18; 623/3.1

(58) Field of Classification Search .................... 600/16, 600/18; 623/3.1
See application file for complete search history.

(56) References Cited

U.S. PATENT DOCUMENTS

| 283,660 A | 8/1883 | Reed |
|---|---|---|
| 929,571 A | 7/1909 | Dubied |
| 1,576,397 A | 7/1925 | Yanagi |
| 1,719,316 A | 7/1929 | Appleton |
| 3,467,077 A | 9/1969 | Cohen, Leah |

(Continued)

FOREIGN PATENT DOCUMENTS

AU   2003277983   6/2008

(Continued)

OTHER PUBLICATIONS

Seymour Furman et al., "Cardiac Support by Periaortic Diastolic Augmentation", New York Journal of Medicine, Aug. 1, 1970, pp. 1964-1969.

(Continued)

Primary Examiner — Niketa I Patel
Assistant Examiner — Joseph Stoklosa
(74) Attorney, Agent, or Firm — Faegre & Benson LLP (57) ABSTRACT

A fluid pressure generating means (10) for a heart assist device having blood pumping means. The pressure generating means (10) includes a housing (11), defining an interior volume (18), and having a substantially rigid first housing portion (12), a substantially rigid second housing portion (14), a flexible third housing portion (16) extending between the first (12) and second (14) housing portions and an inlet/outlet port (15) adapted for fluid communication with the blood pumping means. The pressure generating means (10) also includes a fluid filling the housing and a motor (20) disposed within the housing (11) and connected between the first (12) and second (14) housing portions. Actuation of the motor (20) moves the first (12) and second (14) housing portions relative to one another to generate fluid pressure changes at the inlet/outlet port (15). A related heart assist device and method for the treatment of congestive heart failure, myocardial ischemia and like conditions are also disclosed.

20 Claims, 7 Drawing Sheets

U.S. PATENT DOCUMENTS

| | | |
|---|---|---|
| 3,552,383 A | 1/1971 | Krueger et al. |
| 3,597,766 A * | 8/1971 | Buck .................... 623/3.22 |
| 4,014,318 A | 3/1977 | Dockum et al. |
| 4,051,840 A | 10/1977 | Kantrowitz et al. |
| 4,176,411 A | 12/1979 | Runge |
| 4,195,623 A | 4/1980 | Zeff et al. |
| 4,236,482 A | 12/1980 | Gingerich et al. |
| 4,256,094 A | 3/1981 | Kapp et al. |
| 4,277,706 A | 7/1981 | Issacson |
| 4,304,225 A | 12/1981 | Freeman |
| 4,454,891 A | 6/1984 | Dreibelbis et al. |
| 4,457,673 A | 7/1984 | Conley et al. |
| 4,459,977 A | 7/1984 | Pizon et al. |
| 4,515,587 A | 5/1985 | Schiff |
| 4,583,523 A | 4/1986 | Kleinke et al. |
| 4,594,731 A | 6/1986 | Lewkowicz |
| 4,630,597 A | 12/1986 | Kantrowitz et al. |
| 4,676,482 A | 6/1987 | Reece et al. |
| 4,697,574 A | 10/1987 | Karcher et al. |
| 4,763,646 A | 8/1988 | Lekholm |
| 4,771,765 A | 9/1988 | Choy et al. |
| 4,809,676 A | 3/1989 | Freeman |
| 4,813,952 A | 3/1989 | Khalafalla |
| 4,822,357 A | 4/1989 | Forster et al. |
| 4,881,939 A | 11/1989 | Newman |
| 4,957,477 A | 9/1990 | Lundback |
| 4,979,936 A | 12/1990 | Stephenson et al. |
| 5,089,017 A | 2/1992 | Young et al. |
| 5,169,378 A | 12/1992 | Figuera |
| 5,197,980 A | 3/1993 | Gorshkov et al. |
| 5,205,810 A | 4/1993 | Guiraudon et al. |
| 5,222,980 A | 6/1993 | Gealow |
| 5,267,940 A | 12/1993 | Moulder |
| 5,273,518 A | 12/1993 | Lee |
| 5,290,249 A | 3/1994 | Foster et al. |
| 5,300,111 A | 4/1994 | Panton et al. |
| 5,337,752 A | 8/1994 | Reeves |
| 5,344,385 A * | 9/1994 | Buck et al. .................... 600/16 |
| 5,360,445 A | 11/1994 | Goldowsky |
| 5,372,573 A | 12/1994 | Habib |
| 5,429,584 A | 7/1995 | Chiu |
| 5,447,523 A | 9/1995 | Schaldach |
| 5,453,076 A | 9/1995 | Kiyota et al. |
| 5,511,551 A | 4/1996 | Sano et al. |
| 5,554,177 A | 9/1996 | Kieval et al. |
| 5,569,156 A | 10/1996 | Mussivand |
| 5,593,414 A | 1/1997 | Shipp et al. |
| 5,607,378 A | 3/1997 | Winston |
| 5,647,380 A | 7/1997 | Campbell et al. |
| 5,722,930 A | 3/1998 | Larson, Jr. et al. |
| 5,792,195 A | 8/1998 | Carlson et al. |
| 5,814,012 A | 9/1998 | Fleenor et al. |
| 5,820,542 A | 10/1998 | Dobak, III et al. |
| 5,827,171 A | 10/1998 | Dobak, III et al. |
| 5,843,170 A | 12/1998 | Ahn |
| 5,975,140 A | 11/1999 | Lin |
| 5,980,448 A | 11/1999 | Heilman et al. |
| 6,030,336 A | 2/2000 | Franchi |
| 6,045,496 A | 4/2000 | Pacella et al. |
| 6,066,085 A | 5/2000 | Heilman et al. |
| 6,132,363 A | 10/2000 | Freed et al. |
| 6,132,636 A | 10/2000 | Singh et al. |
| 6,210,318 B1 | 4/2001 | Lederman |
| 6,210,319 B1 | 4/2001 | Williams et al. |
| 6,226,843 B1 | 5/2001 | Crainich |
| 6,251,061 B1 | 6/2001 | Hastings et al. |
| 6,406,422 B1 | 6/2002 | Landesberg |
| 6,432,039 B1 | 8/2002 | Wardle |
| 6,471,633 B1 | 10/2002 | Freed |
| 6,553,263 B1 | 4/2003 | Meadows et al. |
| 6,572,534 B1 | 6/2003 | Milbocker et al. |
| 6,585,635 B1 | 7/2003 | Aldrich |
| 6,616,596 B1 | 9/2003 | Milbocker |
| 6,626,821 B1 | 9/2003 | Kung et al. |
| 6,643,548 B1 | 11/2003 | Mai et al. |
| 6,808,483 B1 | 10/2004 | Ortiz et al. |
| 6,808,484 B1 | 10/2004 | Peters et al. |
| 6,984,201 B2 | 1/2006 | Khaghani et al. |
| 7,169,109 B2 | 1/2007 | Jansen et al. |
| 7,306,558 B2 * | 12/2007 | Peters et al. .................... 600/16 |
| 7,347,811 B2 | 3/2008 | Peters et al. |
| 7,357,771 B2 | 4/2008 | Peters et al. |
| 7,513,864 B2 | 4/2009 | Kantrowitz et al. |
| 7,740,575 B2 * | 6/2010 | Peters et al. .................... 600/16 |
| 7,765,003 B2 | 7/2010 | Peters et al. |
| 2001/0016676 A1 | 8/2001 | Williams et al. |
| 2003/0105497 A1 | 6/2003 | Zhu et al. |
| 2004/0010180 A1 | 1/2004 | Scorvo |
| 2004/0073080 A1 | 4/2004 | Peters et al. |
| 2004/0097783 A1 | 5/2004 | Peters et al. |
| 2004/0097784 A1 | 5/2004 | Peters et al. |
| 2004/0147803 A1 | 7/2004 | Hegde et al. |
| 2004/0152945 A1 | 8/2004 | Kantrowitz et al. |
| 2006/0052866 A1 | 3/2006 | Gilles et al. |
| 2007/0021830 A1 | 1/2007 | Peters |
| 2007/0093684 A1 | 4/2007 | Peters |
| 2007/0129796 A1 | 6/2007 | Miller |
| 2007/0135677 A1 | 6/2007 | Miller et al. |
| 2007/0167898 A1 | 7/2007 | Peters et al. |
| 2008/0139873 A1 | 6/2008 | Peters et al. |
| 2008/0167515 A1 | 7/2008 | Peters et al. |
| 2008/0194905 A1 | 8/2008 | Walsh |
| 2010/0292528 A1 | 11/2010 | De Plater |

FOREIGN PATENT DOCUMENTS

| | | |
|---|---|---|
| DE | 1541311 | 9/1969 |
| EP | 0 216 042 A1 | 4/1987 |
| EP | 0 216 042 B1 | 4/1987 |
| EP | 0080348 B2 | 5/1988 |
| EP | 0363203 | 4/1990 |
| EP | 0364799 | 4/1990 |
| EP | 0601804 | 6/1994 |
| EP | 1129736 | 9/2001 |
| FR | 2 458 288 | 1/1981 |
| FR | 2645739 | 10/1990 |
| FR | 2 767 874 | 3/1999 |
| GB | 2422114 | 4/2008 |
| JP | 06-510461 | 11/1994 |
| JP | 9-502376 | 3/1997 |
| JP | 9-503933 | 4/1997 |
| JP | 10328297 | 12/1998 |
| JP | H11-285529 | 10/1999 |
| JP | 2000-000299 | 1/2000 |
| JP | 2000-510006 | 8/2000 |
| JP | 2001-276213 | 10/2001 |
| JP | 2003-135497 | 5/2003 |
| WO | WO 92/08500 | 5/1992 |
| WO | WO 93/08874 | 5/1993 |
| WO | WO 95/05122 | 2/1995 |
| WO | WO 95/28127 | 10/1995 |
| WO | WO 97/40755 | 11/1997 |
| WO | WO 98/05289 | 2/1998 |
| WO | WO 98/14239 | 4/1998 |
| WO | WO 98/51367 | 11/1998 |
| WO | WO 99/02213 | 1/1999 |
| WO | WO 99/04833 | 2/1999 |
| WO | WO 99/45981 | 9/1999 |
| WO | WO 00/012168 | 3/2000 |
| WO | WO 00/76288 | 12/2000 |
| WO | WO 01/13974 | 3/2001 |
| WO | WO 01/83001 | 11/2001 |
| WO | WO 02/024254 | 3/2002 |
| WO | WO 02/024255 | 3/2002 |
| WO | WO 02/076305 | 10/2002 |
| WO | WO 03/028787 | 4/2003 |
| WO | WO 2004/045677 | 6/2004 |
| WO | WO 2005/041783 | 5/2005 |
| WO | WO 2005/042063 | 5/2005 |
| WO | WO 2005/044338 | 5/2005 |
| WO | WO 2005/110512 | 11/2005 |
| WO | WO 2008/053469 | 5/2008 |
| WO | WO 2008/071223 | 6/2008 |

OTHER PUBLICATIONS

J.L. Stewart, "Aortic Cuff a Cardiac Assistance Device", Polytechnic Institute of Brooklyn, 1968, pp. 9-108.

Hiroshi Odaguchi et al., "Experimental Study of Extraaortic Balloon Counterpulsation as a Bridge to Other Mechanical Assists" ASAIO Journal, pp. 190-194, vol. 42, No. 3, Lippincott Williams & Wilkins/ASAIO, Hagerstown, MD, May 1, 1996. cited by other.

"Use of Heart Valve Sounds as Input to Cardiac Assist Devices", Research Disclosures, Mar. 1995.

Luisada et al., On the Function of the Aortic Valve and the Mechanism of the First and Second Sounds, Japanese Heart Journal, vol. 18(1), Jan. 1977, pp. 81-91.

International Search Report issued in PCT/AU00/00654, mailed Aug. 18, 2000, 5 pages.

International Search Report issued in PCT/AU2001/01187, mailed Nov. 5, 2001, 3 pages.

International Preliminary Examination Report issued in PCT/AU2001/01187, completed May 2, 2002, 4 pages.

International Search Report and Written Opinion issued in PCT/AU2007/001188, mailed Oct. 4, 2007, 12 pages.

International Preliminary Report on patentability, Chapter II, issued in PCT/AU2007/001188, completed Mar. 11, 2008, 8 pages.

International Search Report issued in PCT/AU2003/001450, mailed Feb. 2, 2004, 2 pages.

International Preliminary Examination Report issued in PCT/AU2003/001450, completed Mar. 2, 2005, 4 pages.

International Search Report issued in PCT/AU2003/001458, mailed Feb. 5, 2004, 5 pages.

International Preliminary Examination Report issued in PCT/AU2003/001458, completed Mar. 7, 2005, 7 pages.

International Search Report and Written Opinion issued in PCT/AU2004/001483, mailed Nov. 26, 2004, 5 pages.

International Search Report and Written Opinion issued in PCT/AU2004/001484, mailed Nov. 29, 2004, 5 pages.

International Search Report and Written Opinion issued in PCT/AU2004/01485, mailed Feb. 7, 2005, 6 pages.

International Search Report and Written Opinion issued in PCT/AU2004/001486, mailed Jan. 6, 2005, 7 pages.

International Search Report and Written Opinion issued in PCT/AU2004/01487, mailed Jan. 27, 2005, 12 pages.

International Search Report and Written Opinion issued in PCT/AU2004/01488, mailed Dec. 15, 2004, 6 pages.

Supplemental European Search Report issued in EP Application 00934813, mailed Oct. 19, 2006, 2 pages.

Supplemental European Search Report issued in EP 01971489, completed Nov. 22, 2006, 4 pages.

Supplemental European Search Report issued in EP App. No. 04789624, mailed Mar. 6, 2008, 7 pages.

Supplemental European Search Report issued in EP 04789625, mailed Nov. 18, 2009, 6 pages.

Office Action issued in JP Application No. 2004-552261, dated Mar. 2, 2010.

International Search Report issued in PCT/AU2002/000974, Aug. 11, 2003.

International Preliminary Examination Report issued in PCT/AU/000974, completed Aug. 11, 2003.

European Search Report issued in EP App No. 02748447, dated Feb. 6, 2007.

Partial European Search Report issued in EP App No. 02748447, mailed Nov. 20, 2006.

* cited by examiner

FLUID PRESSURE GENERATING MEANS

RELATED INFORMATION

This application is a continuation of co-pending application Ser. No. 10/380,789 filed on Oct. 2, 2003, now U.S. Pat. No. 7,306,558 and which claims priority to Australian Provisional Application No. PR 6690, filed Jul. 30, 2001, and to PCT Application PCT/AU02/00974, filed Jul. 22, 2002 (International Publication No. WO 03/011365).

FIELD OF THE INVENTION

The present invention relates to a fluid pressure generating means for use with a heart assist device.

BACKGROUND OF THE INVENTION

The applicant's international PCT patent application no. PCT/AU00/00654 (International publication no. WO 00/76288) entitled "Heart Assist Devices, Systems and Methods" ("the PCT application") discloses numerous embodiments of a novel heart assist device adapted for implantation into a patient. Broadly speaking, the disclosed heart assist devices include: an aortic compression means adapted, when actuated, to compress an aorta of a patient; a fluid reservoir; and a fluid pressure generating means adapted to pump fluid from the fluid reservoir to the aortic compression means so as to actuate the aortic compression means in counterpulsation with the patient's heart. The relevant portions of the PCT application are incorporated herein by cross-reference.

It is a first object of the present invention to provide improved fluid pressure generating means suitable for use with the aortic compression means described in the PCT application. It is a second object to provide a fluid pressure generating means which may be placed more conveniently into the body of a patient.

SUMMARY OF THE INVENTION

Accordingly, in a first aspect, the present invention provides a fluid pressure generating means for a heart assist device having blood pumping means, the pressure generating means including:

a housing, defining an interior volume, and having a substantially rigid first housing portion, a substantially rigid second housing portion, a flexible third housing portion extending between the first and second housing portions and an inlet/outlet port adapted for fluid communication between the interior volume and the blood pumping means;

a fluid filling the housing; and a motor or other actuator means disposed within the interior volume of the housing and connected between the first and second housing portions, wherein actuation of the motor or other actuator means moves the first and second housing portions relative to one another to generate fluid pressure changes at the inlet/outlet port.

In one preferred form, the third housing portion has an outer edge about its periphery and inner edge about an opening and is joined along the outer and the inner edge to the first and second housing portions respectively.

In another preferred form, the third housing portion is connected to only one of the first and second housing portions and abuts against the other of the first and second housing portions.

The blood pumping means is preferably adapted to displace blood in the aorta, more specifically the ascending aorta, and preferably by compressing or deforming the aorta of a patient in counter-pulsation with the patient's heart. More preferably, the blood pumping means is adapted to displace blood from the ascending aorta of the patient. In an alternative arrangement, the fluid pressure generating means can be used to drive a conventional left ventricular assist device or an extra-ventricular co-pulsation heart compression device. In such an arrangement suitable valves are used to ensure the correct direction of blood flow through a pumping chamber driven by the fluid pressure generating means.

In a further preferred form, one of the first and second housing portions is moveable and the other of the first and second housing portions is fixed, the moveable housing portion being exposed to the outside of the heart assist device and adapted to interface with the lung of a patient.

In a yet further preferred form, one of the first and second housing portions is moveable and the other of the first and second housing portions is fixed, the moveable housing portion not being exposed to the outside of the heart assist device and the device including a flexible compliance chamber. The compliance chamber is desirably in contact with the lung of a patient.

The actuating means desirably includes a nut coupled to one of the first and second housing portions and a threaded shaft coupled to the other of the first and second housing portions, the threaded shaft and the nut being threadedly engaged and the motor being adapted to rotate the nut relative to the threaded shaft. In one arrangement, the nut is connected to the moveable one of the first and second housing portions and the threaded shaft is connected to the fixed one of the first and second housing portions. In another arrangement, the threaded shaft is connected to the moveable one of the first and second housing portions and the nut is connected to the fixed one of the first and second housing portions.

In an embodiment, the outflow of the fluid from the inlet/outlet port is axial to the housing. In another embodiment, the outflow of the fluid from the inlet/outlet port is radial to the housing. In a further embodiment, the outflow of the fluid from the inlet/outlet port is tangential to the housing.

A surface of the device is preferably curved to fit snugly with the chest wall and/or mediastinum and/or diaphragm of a patient.

The blood pumping means is preferably in the form of a fluid operated cuff adapted to surround the patient's aorta.

The fluid filling the housing is preferably a liquid. The liquid is preferably an oil or saline. The oil is preferably a silicone oil and desirably has viscosity between 10 and 100 centistokes, most desirably between 10 and 30 centistokes.

In a second aspect, the present invention provides a heart assist device including:

a blood pumping means adapted, when actuated, to cause or assist the movement of blood around the patient's vasculature;

a fluid reservoir;

a fluid pressure generating means adapted to pump fluid from the fluid reservoir to the blood pumping means; and a housing containing both the fluid reservoir and the fluid pressure generating means that is so shaped and dimensioned as to be adapted to lie in the plueral cavity, adjacent to the lung, when the blood pumping means is functionally positioned within the patient.

In a third aspect, the present invention provides a method for the treatment of congestive heart failure, myocardial ischemia and like conditions, the method comprising:

inserting into the plueral cavity within the chest (preferably the right chest) of a patient, and adjacent to the lung, a housing containing a fluid reservoir and a fluid pressure generating means adapted to pump fluid from the fluid reservoir to blood pumping means functionally placed in the patient so as to cause or assist the movement of blood around the patient's vasculature.

Until now most implanted heart assist devices have been placed in the abdominal cavity of a patient. This is disadvantageous as it complicates the surgical procedure and is unduly invasive for the patient. The few proposals for placement of such a device in the chest cavity have proposed the placement of the device against the inside of the chest wall so that the device can be wired to the ribs of the patient. It was apparently felt that this was necessary to support the weight of the device and to prevent it from moving around in the patient. The present inventors have found that the device may be placed against the mediastinum directly adjacent the patient's heart and attached to surrounding soft tissue. The device will thus lie in the plueral cavity, adjacent to the lung. The device preferably lies in a sagittal plane within the patient's body. Desirably, the device will not touch the inside surface of the chest wall at all. This placement will reduce pain for the patient and make placement of the device easier for the surgeon implanting the device.

Preferably, the blood pumping means referred to in the above method is adapted to compress the aorta of a patient in counter-pulsation with the patient's heart. More preferably, the blood pumping means is adapted to compress the ascending aorta of the patient.

In a fourth aspect, the present invention provides a heart assist device including:

a blood pumping means adapted, when actuated, to cause or assist the movement of blood around the patient's vasculature;

a fluid reservoir; and a fluid pressure generating means driven by an electric motor and adapted to pump a liquid from the fluid reservoir to the blood pumping means;

the electric motor having a cogging torque which is sufficiently low that the natural systolic blood pressure of the patient is sufficient to cause liquid in the blood pumping means to be returned to the fluid reservoir in the event that the electric motor stops.

BRIEF DESCRIPTION OF THE DRAWINGS

Preferred embodiments of the invention will now be described, by way of examples only, with reference to the accompanying drawings in which:

FIG. 4b is an underside perspective view of a housing portion of the fluid pressure generating means shown in FIG. 4a;

FIG. 4c is a schematic longitudinal sectional view of the fluid pressure generating means shown in FIG. 4a.

DETAILED DESCRIPTION OF THE PREFERRED EMBODIMENTS

Figure 1:
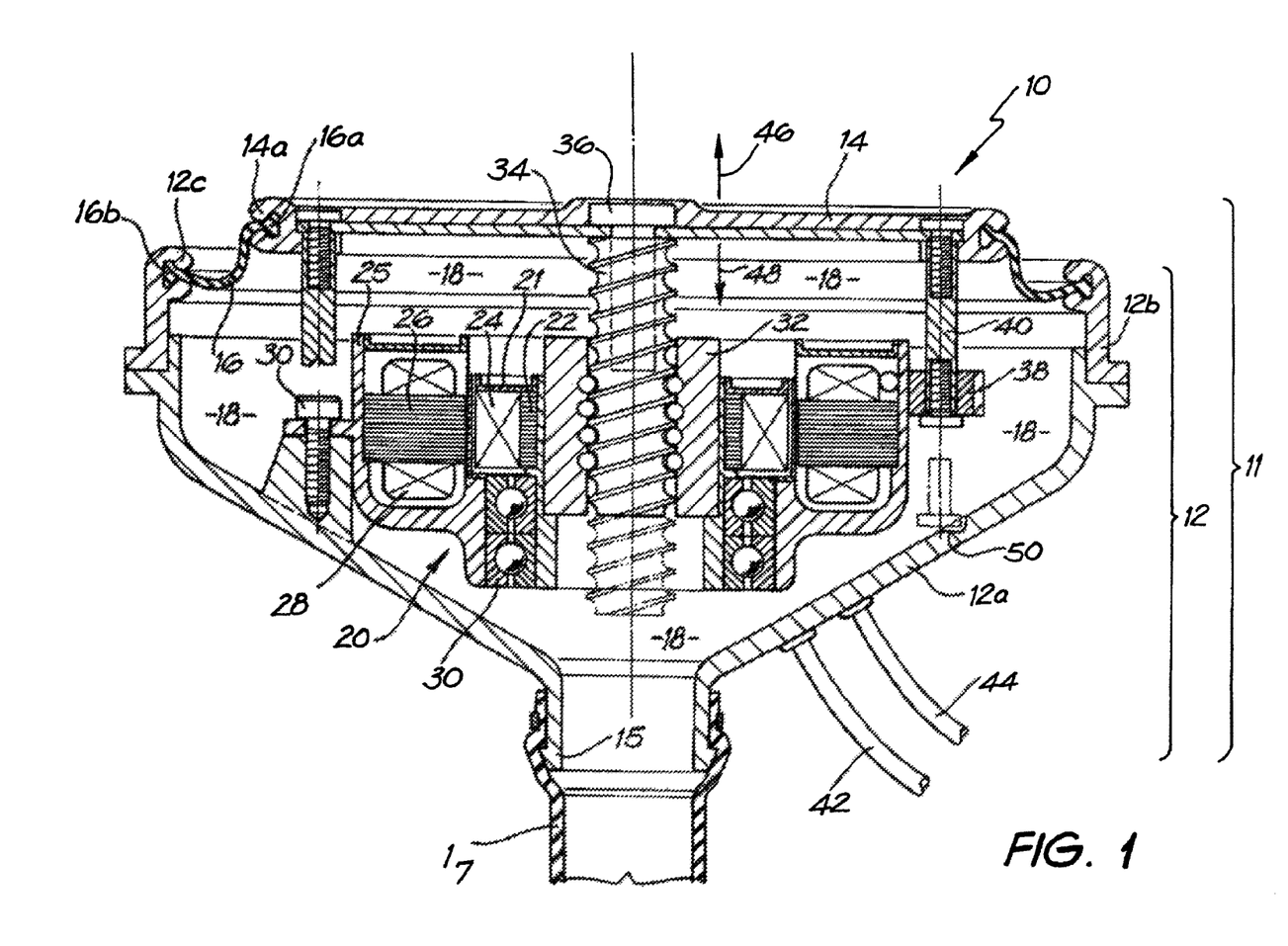
FIG. 1 is a schematic longitudinal sectional view of a first embodiment of a fluid pressure generating means according to the invention.

Referring firstly to FIG. 1, there is shown a schematic longitudinal sectional view of a first embodiment of a fluid pressure generating means according to the invention, in the form of pump 10. The pump 10 includes a housing, indicated generally by the reference numeral 11, comprising a substantially rigid bell-shaped first housing portion 12, a substantially rigid flat circular second housing portion 14 and a flexible third housing portion or membrane 16.

The first, second and third housing portions 12, 14 and 16 together define an external boundary of the housing 11 around an interior volume denoted 18, which is filled with a silicone oil. The second housing portion 12 is itself formed from a cone-shaped portion 12a which is sealingly connected, after assembly of the pump 10, to a cylindrical portion 12b.

The cone-shaped portion 12a also includes an inlet/outlet port 15, which is connected in fluid communication with an aortic compression means or blood pumping means (not shown) by a conduit 17.

The membrane 16 is substantially annular in configuration and has enlarged inner and outer edges 16a and 16b which are sealingly received in corresponding circumferential recesses 12c and 14a provided in the first and second housing portions 12 and 14 respectively.

The pump 10 also includes an electric motor, indicated generally by the reference numeral 20, within the interior volume 18 of the housing 11. The motor includes a rotor 21, rotor laminations 22, magnets 24, stator 25, stator laminations 26, end windings 28 and bearings 30.

The stator 25 is fixed to the housing portion 12a by a number of screws 30 (only one shown). The rotor 21 is fixed to a nut 32, which is itself threadedly engaged with a threaded shaft 34 through ball bearings (not shown). The shaft 34 is fixed to the housing portion 14 by screw 36. The stator 25 also includes a number of guide journals 38 (only one shown) through which are guided a corresponding number of shafts 40 that depend from the housing portion 14.

Power and control signals are fed to the motor 20 through lines 42 and 44 respectively.

The operation of the pump 10 will now be described. Energising the motor 20 to rotate in a first direction rotates the nut 32 relative to the threaded shaft 34 which causes the threaded shaft 34 to move in a direction parallel to its longitudinal axis in a first direction indicated by arrow 46. FIG. 1 shows the shaft 34 at the end of its travel in this direction and after driving the housing portion 14 away from the housing portion 12 to increase the interior volume 18 and cause a suction or negative pressure at the inlet/outlet port 15. This suction actively deflates the aortic compression means (not shown).

Energising the motor to rotate in the opposite direction causes the threaded shaft 34 to move parallel to the longitudinal axis in the opposite direction indicated by arrow 48 and draw the portion 14 towards the housing portion 12. The end limit of travel in this direction is indicated in phantom in FIG. 1 and, with reference to which it should be noted that, the guide shaft 40 abuts the inner surface of the housing portion 12a at the limit of its travel at recess 50. Drawing the flexible portion 14 towards the housing portion 12 reduces the interior volume 18 which causes a positive pressure at the inlet/outlet port 15 and drives fluid from the interior volume 18 to inflate the aortic compression means.

The motor 20 is actuated cyclicly in this manner in counterpulsation with the patient's heart in response to signals received from an ECG monitor or systemic arterial pressure, as disclosed in the PCT application.

Figure 2:
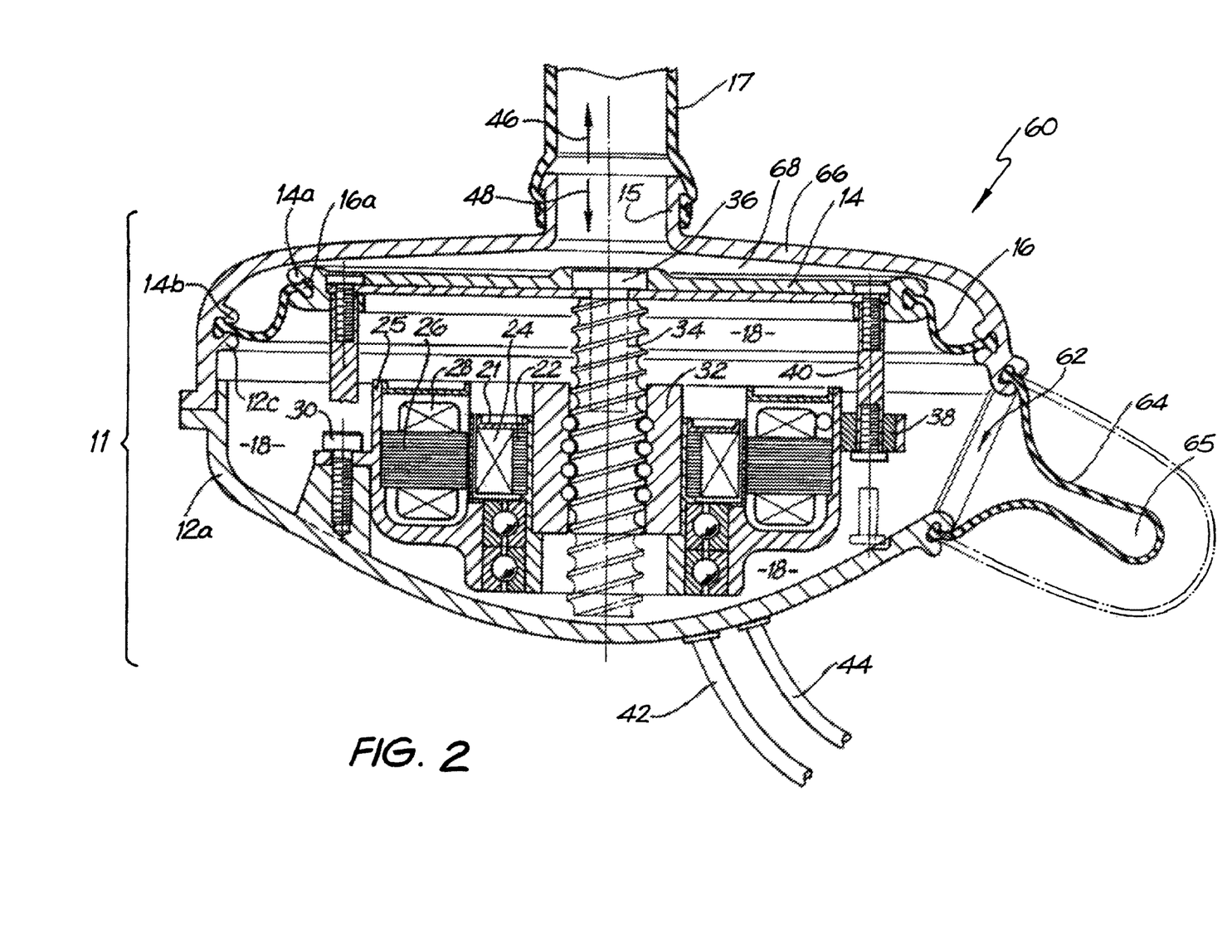
FIG. 2 is a schematic longitudinal sectional view of a second embodiment of a fluid pressure generating means according to the invention.

Referring now to FIG. 2, there is shown a schematic longitudinal sectional view of a second embodiment of a fluid pressure generating means according to the invention, in the form of pump 60. The pump 60 is similar to the pump 10 shown in FIG. 1 and like features are indicated with like reference numerals. Differences between the pumps 10 and 60 are described in detail below.

Firstly, the housing portion 12a of the pump 60 includes an opening 62 sealed by a second flexible membrane 64 which forms a compliance chamber 65. The chamber 65 is in fluid communication with the interior volume 18. Secondly, the inlet/outlet port 15 is provided in a further housing portion 66 which is sealed with respect to the side of the second housing portions 14 and third housing portion 16 that is remote the motor 20. The housing portion 66 creates, in conjunction with the housing portions 14 and 16, a second interior volume 68 in fluid communication with the aortic compression means or blood pumping means (not shown) via conduit 17.

The operation of the pump 60 is similar to that as described with reference to the pump 10 with the exception that the movement of the housing portion 14 causes volume changes in the second interior volume 68 which in turn inflates and deflates the aortic compression means. The movement of the housing portion 14 also causes fluid movement in the part of the interior volume 18 within the first, second and third housing portions 12, 14 and 16 and these changes cause an identical volume change in the interior of the compliance chamber 65, which is shown having a decreased volume in response to the compression means being inflated. The chamber 65 will have an increased volume in response to the compression means being deflated, as is shown in phantom.

As the interior volumes 18 and 68 are maintained sealed from one another by the second and third housing portions 14 and 16, the pump 60 can be configured to use different fluids in each of the interior volumes 18 and 60, as desired. For example, a saline solution can be used in the interior volume 68 and a lubricating oil can be used in the interior volume 18 which contains the motor 20.

Figure 3:
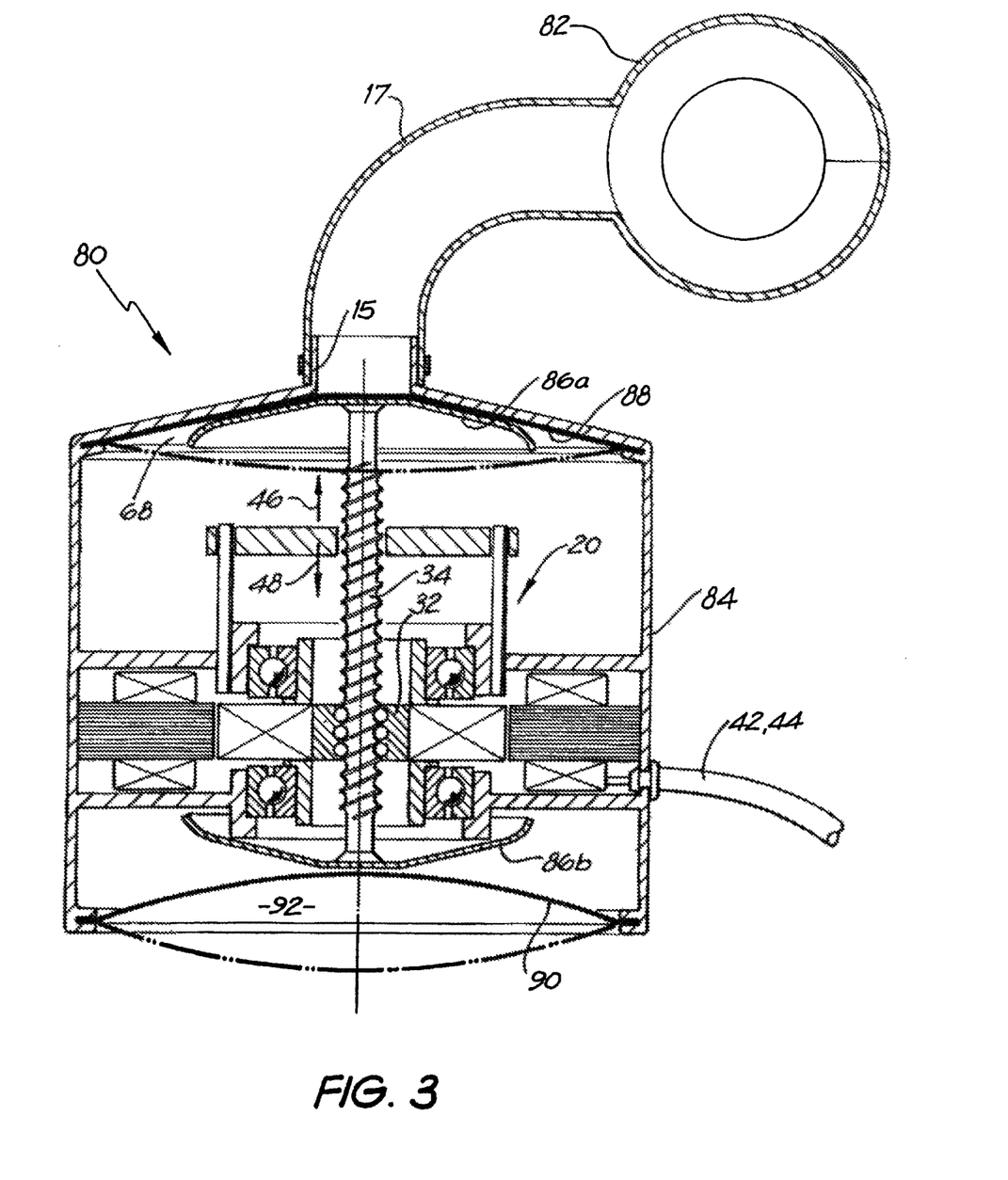
FIG. 3 is a schematic longitudinal sectional view of a third embodiment of a fluid pressure generating means according to the invention connected to a heart assist device.

FIG. 3 is a schematic cross sectional side view of a third embodiment of a fluid pressure generating means according to the invention, in the form of pump 80. The pump 80 is shown connected to an aortic compression means or blood pumping means in the form of cuff 82. The pump 80 is similar to the pump 60 described in relation to FIG. 2 and like reference numerals will be used to indicate like features. Differences between the pumps 60 and 80 are described in detail below.

Firstly, the pump 80 has a first external substantially rigid cylindrical housing portion 84, a pair of second internal substantially rigid housing portions 86a and 86b and a third substantially flexible housing portion 88. The latter seals an end of the first housing portion 84. The pump 80 also includes a second flexible housing portion 90 which seals the other end of the second housing portion 84 and forms a compliance chamber 92. Secondly, the second housing portion 86 and the third flexible housing portion 88 abut, but are not connected, to each other.

The operation of the pump 80 is similar to that described with reference to pump 60 in that the motor 20 is energised to reciprocally drive the threaded shaft 34 and thus the second housing portion 86a in directions 46 and 48 parallel to the longitudinal axis of the threaded shaft 34.

FIG. 3 shows the pump 80 in a position after movement of the second housing portion 86a in the direction 46 and driving fluid from the second interior volume 68 into the cuff 82 to inflate same. In this position, the second membrane of 64 is drawn into the interior of the second housing portion 84 to maintain the interior volume 18 constant. Driving the threaded shaft 34 in the opposite direction 48 results in the housing portion 86b forcing the membrane 64 to the position shown in phantom which is external the second housing portion 84. This also results in the third housing portion 88 being drawn to the position also shown in phantom to maintain the interior volume 18 constant. As previously described in relation to pump 60, when the third housing portion 86 is in this position fluid is drawn into the second interior volume 68 from the cuff 82 to deflate same.

Figure 4:
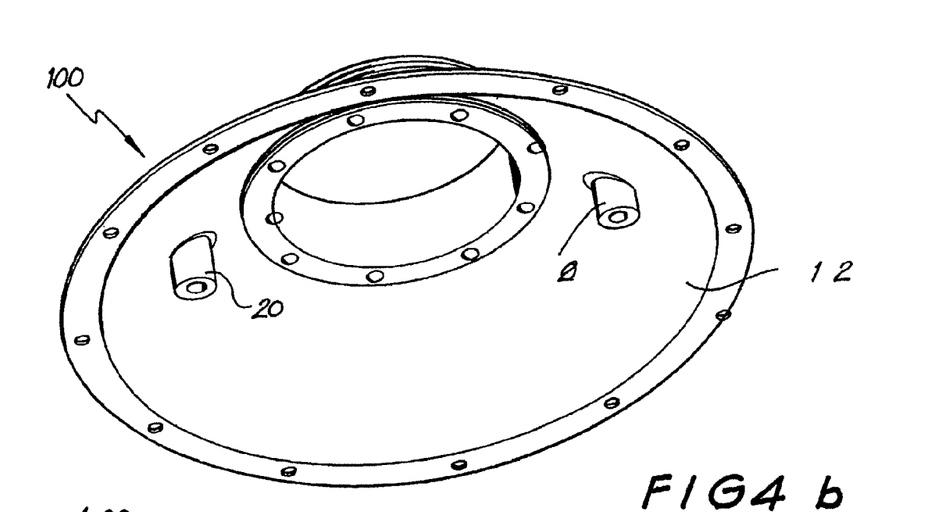
Figure 4A:
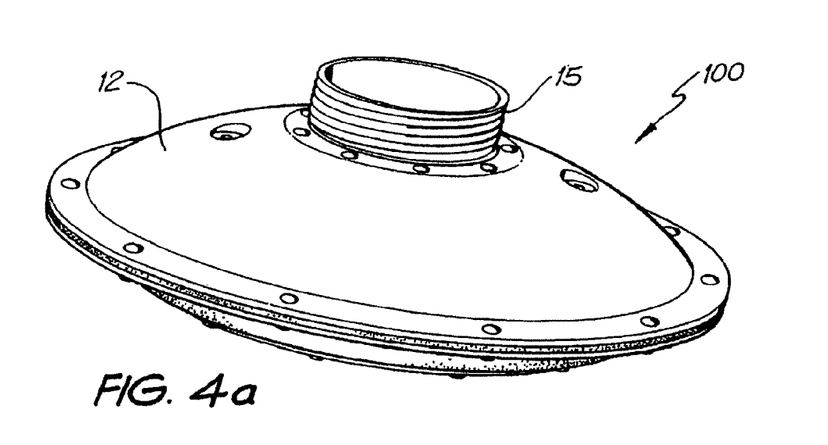
FIG. 4a is a perspective view of a fourth embodiment of a fluid pressure generating means according to the invention.
Figure 4C:
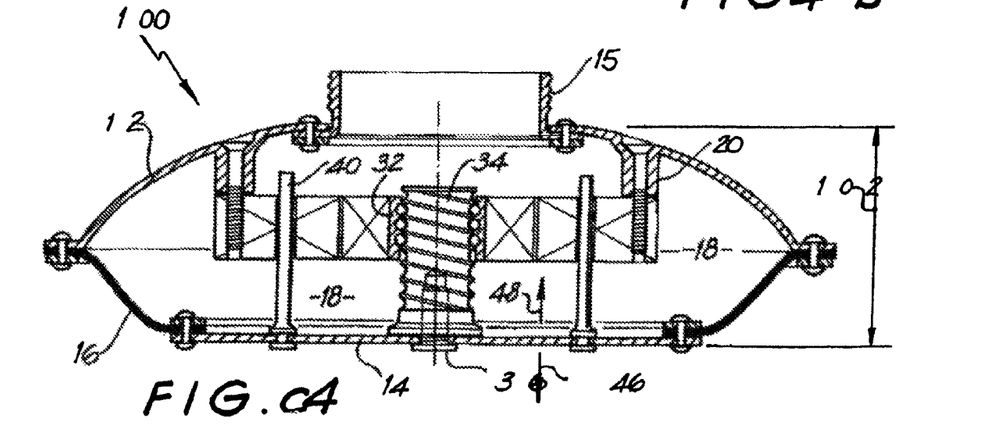

FIGS. 4A to 4C show a fourth embodiment of a fluid pressure generating means according to the invention, in the form of pump 100. The pump 100 is similar to the pump 10 shown in FIG. 1 and like components have been referred to with like reference numerals. However, the pump 100 has been designed to be as thin as possible (dimensions: 82 mm long; 60 mm wide; and 45 mm deep) in order to allow positioning in a patient's chest in contact with the mediastinum adjacent the heart. The pump 100 is placed with the planar housing portion 14 lying in a sagittal plane and with the edge of the housing 100 clear of the inside surface of the chest wall. This orientation is chosen so as to minimise pain and trauma to the patient and also minimise the length of conduit required between the pump 100 and the aortic compression means (not shown). This positioning also assists the surgeon in placing the device.

Figure 5:
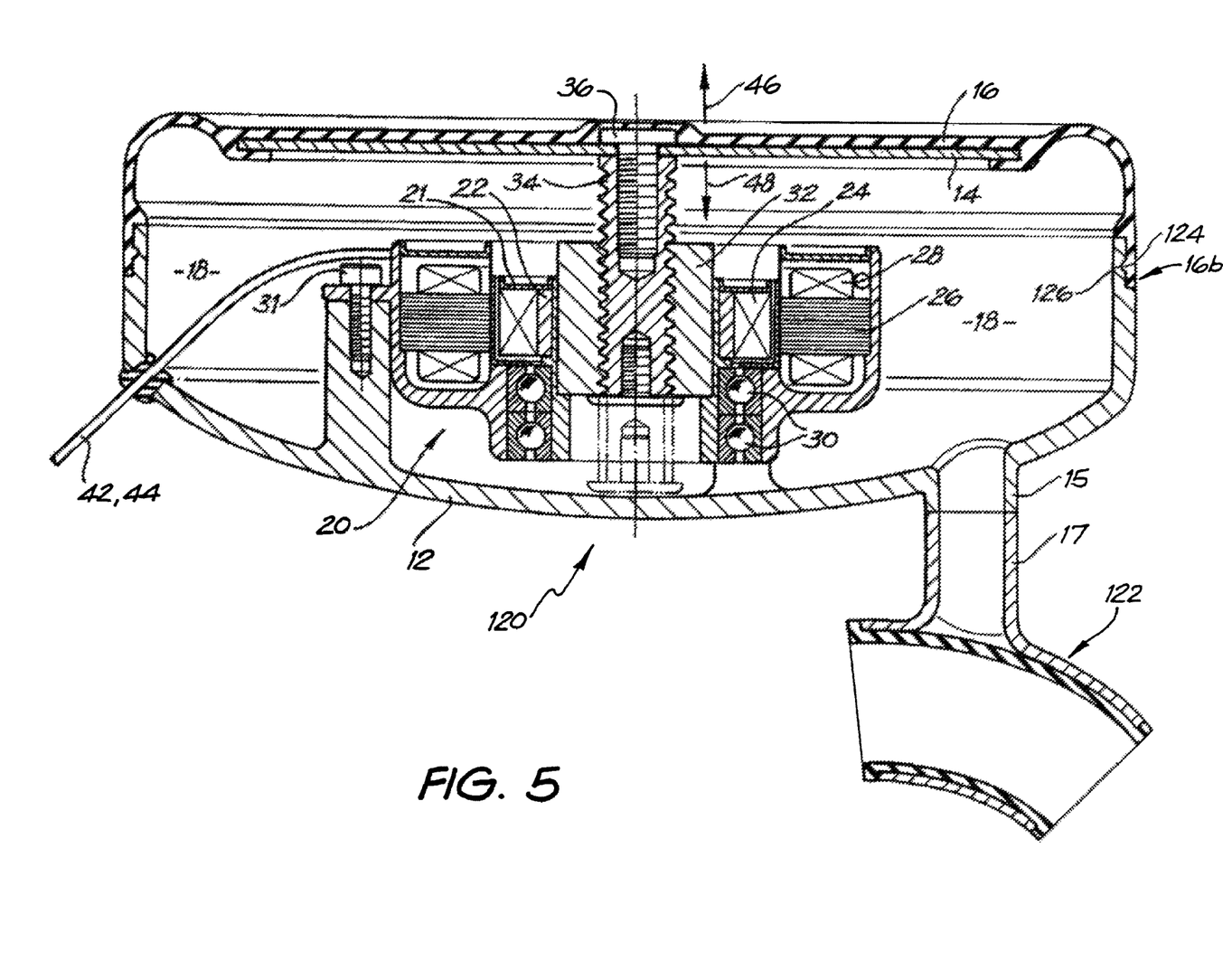
FIG. 5 is a schematic longitudinal sectional view of a fifth embodiment of a heart assist device according to the invention.
Figure 6:
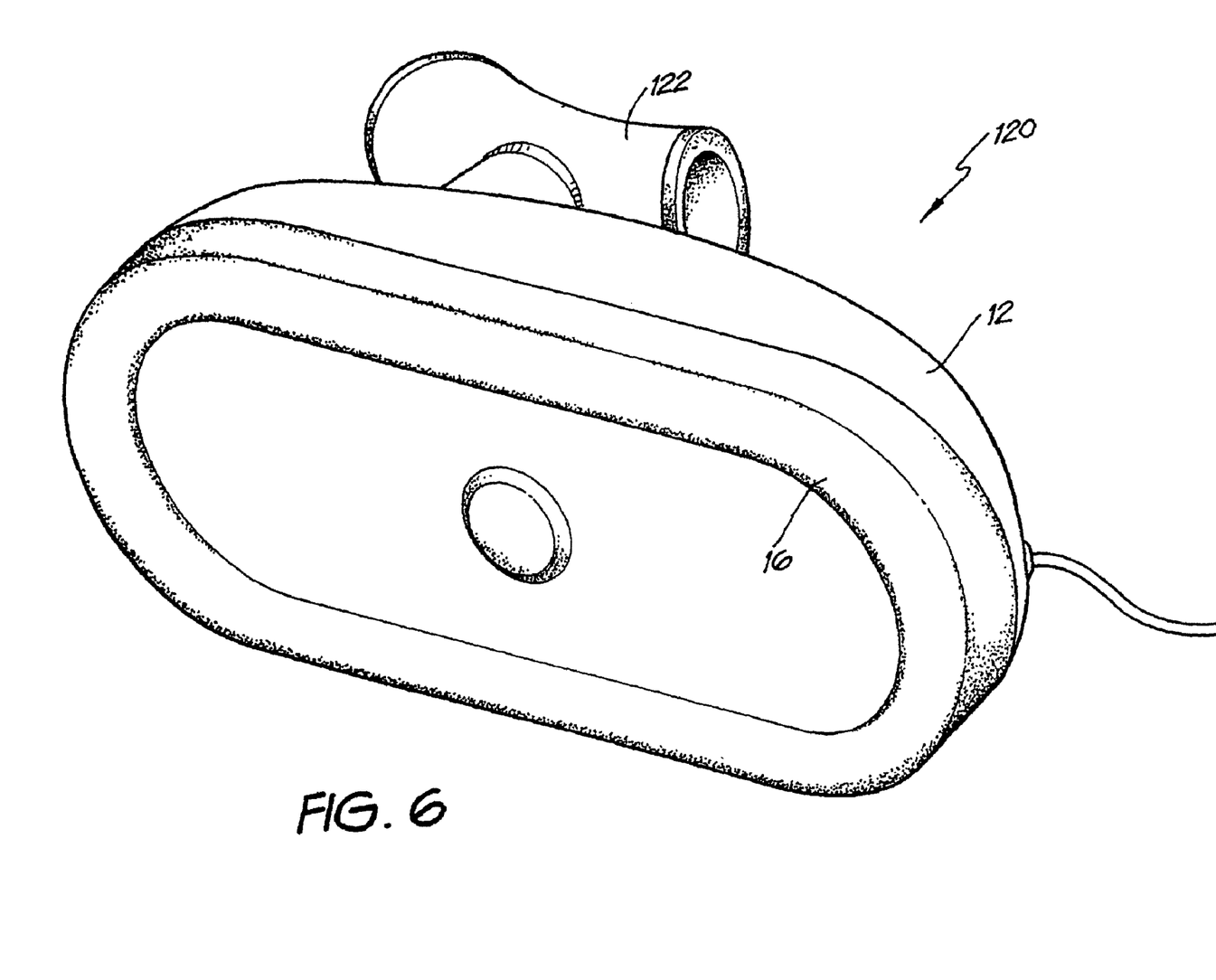
FIG. 6 is a perspective view of the device shown in FIG. 5.
Figure 7:
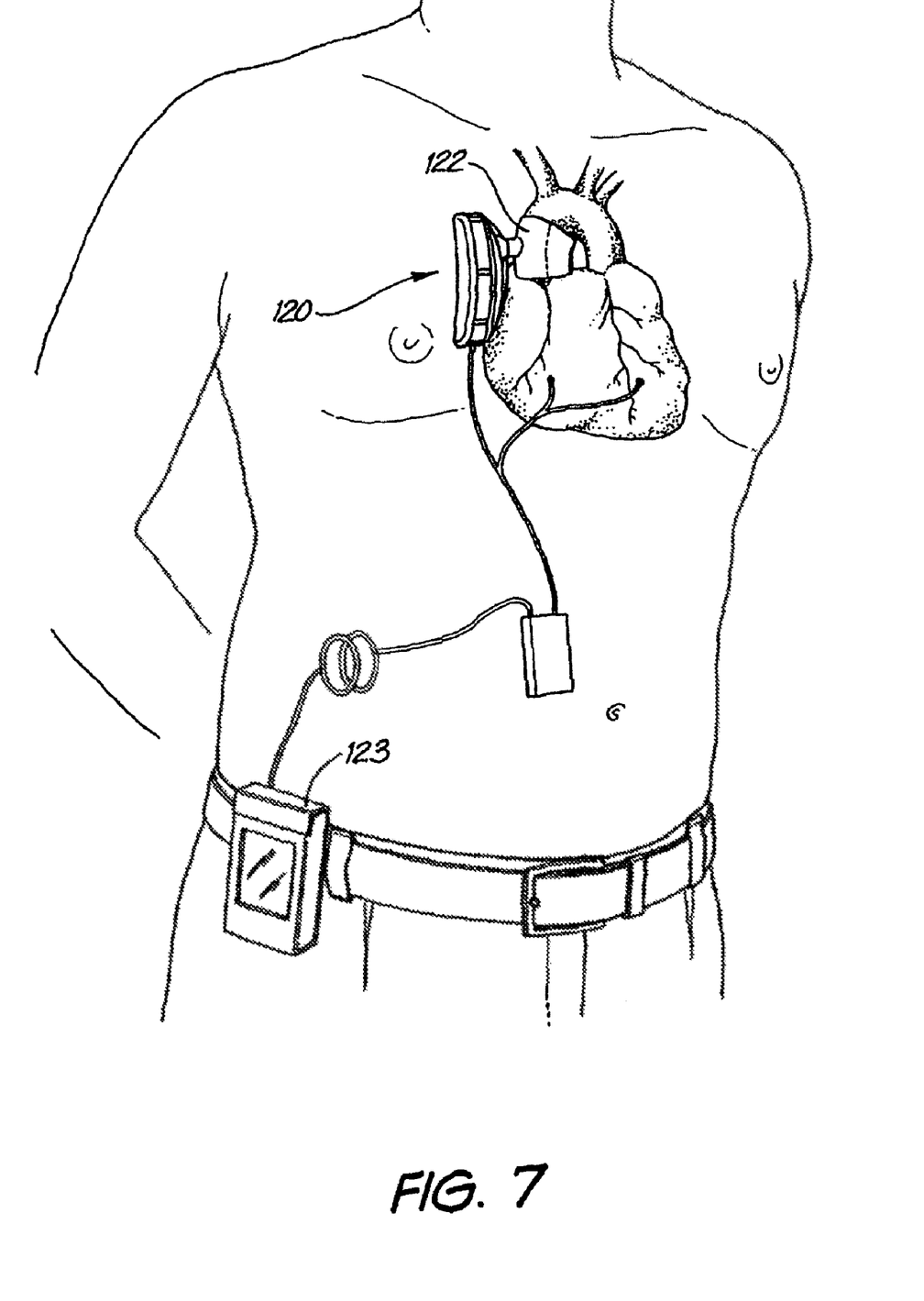
FIG. 7 is a perspective view of the device shown in FIG. 6 after implantation into the pleural cavity, medial to the lung, of a patient.

Referring finally to FIGS. 5 to 7, there is shown a schematic longitudinal sectional view of a fifth embodiment of a fluid pressure generating means according to the invention in the form of pump 120. The pump 120 is shown connected to an aortic compression means or blood pumping means in the form of cuff 122. The construction and operation of the pump 120 is similar to the pump 10 shown in FIG. 1 and like features are indicated with like reference numerals. The size of the pump 120 is similar to the pump 100 shown in FIGS. 4A to 4C, except it is more ovate and has flattened sides (See FIG. 6). The ovate form of the pump 120 and the positioning of the cuff 122 nearer one end allows the device to be placed in the plural cavity, medial to the lung, and lying in a sagittal plane within the patient's body, as is shown in FIG. 7. The pump 120 does not touch the inside surface of the patient's chest wall in this position. FIG. 7 also shows an external battery pack 123 which powers the pump 120.

The main differences between the pumps 10 and 120 are as follows. Firstly, the flexible third housing portion 16 is sealingly connected about its outer edge 16b to the substantially rigid ovate cup-shaped first housing portion 12. The connection and sealing is achieved by a sealing rim 124 on the third portion 16 being snugly received in an annular recess 126 on the first portion 12. Secondly, the substantially rigid flat ovate second housing portion 14 is received within a corresponding recess in the third portion 16, on the interior side of the third portion 16, and is thus within the interior volume 18.

FIG. 5 shows the pump 120 in a position after movement of the second housing portion 14 in the direction 46, which draws fluid into the interior volume 18 from the cuff 122 and deflates same. Driving the threaded shaft 34 in the opposite direction 48 forces the second housing portion 14 towards the motor 20 (see the position of the shaft 34 shown in phantom). As previously described, when this occurs, fluid is forced from the interior volume 18 into the cuff 82 to inflate same.

An advantage of the preferred embodiments of fluid pressure generating means described above is the liquid surrounding the motor is used both as a driving fluid to inflate/deflate the compressions (either directly as per the embodiments of FIGS. 1 and 4 or indirectly as per the embodiment of FIGS. 2 and 3) and as a cooling/lubricating/heat exchanging fluid. The liquid also dampens sound made by the pump mechanism. This simplifies the construction, and minimises the size, of the fluid pressure generating means.

Whilst the fluid pressure generating means will normally actively drive both the inflation and deflation of the aortic compression means, the motor is preferably designed so that the cogging torque of the motor is sufficiently low that the natural systolic blood pressure of the patient is sufficient to deflate the cuff. If the motor is inactivated for any reason with the cuff in an inflated condition (and thus with the aorta partially occluded), this arrangement means that the natural systolic blood pressure will deflate the cuff by pushing fluid from the cuff into the housing and passively driving the second housing portion away from the motor.

It will be appreciated by person skilled in the art that numerous variations and/or modifications can be made to the invention as shown in the specific embodiments without departing from the spirit or scope of invention as broadly described. For example, the embodiments of the invention are not restricted for use with the embodiments of the heart assist device shown in the PCT application. The specific embodiments are, therefore, to be considered in all respects as illustrative and not restrictive.

The invention claimed is:

1. A method of treating congestive failure and myocardial ischemia, the method comprising:
   positioning a fluid pressure generating device in a pleural cavity and adjacent to a lung within a chest of a patient, the fluid pressure generative device comprising:
   (a) a housing having a first housing portion and a second housing portion;
   (b) a fluid disposed within an interior volume of the housing; and
   (c) a motor disposed within the interior volume of the housing;
   coupling the fluid pressure generating device to a blood pumping device positioned in the patient; and
   actuating the motor to move the first and second housing portions relative to one another such that the fluid is pumped from the interior volume of the housing to the blood pumping device, thereby driving the blood pumping device.

2. The method of claim 1, wherein the positioning the fluid pressure generating device in the pleural cavity further comprises positioning the fluid pressure generating device in a right chest of the patient.

3. The method of claim 1, wherein the positioning the fluid pressure generating device in the pleural cavity further comprises positioning the fluid pressure generating device against the mediastinum directly adjacent the patient's heart and attaching the fluid pressure generating device to the surrounding soft tissue.

4. The method of claim 1, wherein the positioning the fluid pressure generating device in the pleural cavity further comprises positioning the fluid pressure generating device such that the fluid pressure generating device lies in a sagittal plane within the patient's body.

5. The method of claim 1, wherein the positioning the fluid pressure generating device in the pleural cavity further comprises positioning the fluid pressure generating device such that the fluid pressure generating device does not touch the inside surface of the chest wall.

6. The method of claim 1, wherein the blood pumping device is configured to displace blood in the aorta of the patient in counter-pulsation with the patient's heart.

7. The method of claim 6, wherein the blood pumping device is configured to displace blood in the ascending aorta of the patient.

8. A method of treating congestive failure and myocardial ischemia, the method comprising:
   positioning a housing in a pleural cavity and adjacent to a lung within a chest of a patient, the housing comprising:
   (a) fluid pressure generating means disposed within the housing;
   (b) a fluid reservoir disposed within the housing; and
   (c) a motor disposed within the housing;
   coupling the housing to a blood pumping device positioned in the patient; and
   actuating the motor to actuate the fluid pressure generating means to pump fluid from the housing to the blood pumping device, thereby driving the blood pumping device.

9. The method of claim 8, wherein the positioning the housing in the pleural cavity further comprises positioning the housing in a right chest of the patient.

10. The method of claim 8, wherein the positioning the housing in the pleural cavity further comprises positioning the housing against the mediastinum directly adjacent the patient's heart and attaching the housing to the surrounding soft tissue.

11. The method of claim 8, wherein the positioning the housing in the pleural cavity further comprises positioning the housing such that the housing lies in a sagittal plane within the patient's body.

12. The method of claim 8, wherein the positioning the housing in the pleural cavity further comprises positioning the housing such that the housing does not touch the inside surface of the chest wall.

13. The method of claim 8, wherein the blood pumping device is configured to displace blood in the aorta of the patient in counter-pulsation with the patient's heart.

14. The method of claim 13, wherein the blood pumping device is configured to displace blood in the ascending aorta of the patient.

15. A method of treating congestive failure and myocardial ischemia, the method comprising:
   positioning a fluid pressure generating device in a pleural cavity and adjacent to a lung within a chest of a patient, the fluid pressure generative device comprising:
   (a) a housing having a first housing portion and a second housing portion;
   (b) a fluid disposed within an interior volume of the housing; and
   (c) a motor disposed within the interior volume of the housing; and
   coupling the fluid pressure generating device to a blood pumping device positioned in the patient,
   wherein the motor is configured to move the first and second housing portions relative to one another such that the fluid is pumped from the interior volume of the housing to the blood pumping device, thereby driving the blood pumping device.

16. The method of claim 15, wherein the positioning the fluid pressure generating device in the pleural cavity further comprises positioning the fluid pressure generating device in a right chest of the patient.

17. The method of claim 15, wherein the positioning the fluid pressure generating device in the pleural cavity further comprises positioning the fluid pressure generating device against the mediastinum directly adjacent the patient's heart and attaching the fluid pressure generating device to the surrounding soft tissue.

18. The method of claim 15, wherein the positioning the fluid pressure generating device in the pleural cavity further comprises positioning the fluid pressure generating device such that the fluid pressure generating device lies in a sagittal plane within the patient's body.

19. The method of claim 15, wherein the positioning the fluid pressure generating device in the pleural cavity further comprises positioning the fluid pressure generating device such that the fluid pressure generating device does not touch the inside surface of the chest wall.

20. The method of claim 15, wherein the blood pumping device is configured to displace blood in the aorta of the patient in counter-pulsation with the patient's heart.

* * * * *